United States Patent
Node et al.

(10) Patent No.: US 8,105,842 B2
(45) Date of Patent: Jan. 31, 2012

(54) INTERLEUKIN-13 AS A CARDIOVASCULAR DISEASE MARKER

(75) Inventors: Koichi Node, Takarazuka (JP); Kenji Izuhara, Saga (JP); Tetsuaki Hirase, Ogi (JP); Yuki Nishimura, Saga (JP)

(73) Assignee: Saga University, Saga (JP)

( * ) Notice: Subject to any disclaimer, the term of this patent is extended or adjusted under 35 U.S.C. 154(b) by 390 days.

(21) Appl. No.: 11/355,089

(22) Filed: Feb. 16, 2006

(65) Prior Publication Data

US 2006/0188504 A1 Aug. 24, 2006

(30) Foreign Application Priority Data

Feb. 21, 2005 (JP) ................................. 2005-044644

(51) Int. Cl.
*G01N 33/577* (2006.01)
*C07K 16/24* (2006.01)
*C07K 14/54* (2006.01)

(52) U.S. Cl. .................................. 436/501; 530/388.23

(58) Field of Classification Search .......................... None
See application file for complete search history.

(56) References Cited

U.S. PATENT DOCUMENTS

| 5,853,697 | A * | 12/1998 | Strober et al. | 424/9.2 |
| 6,495,593 | B1 * | 12/2002 | Bagchi et al. | 514/456 |
| 6,664,227 | B1 * | 12/2003 | Wynn et al. | 514/8 |
| 7,572,920 | B2 * | 8/2009 | Kuroita et al. | 548/132 |

FOREIGN PATENT DOCUMENTS

| WO | WO-03/090776 A1 | 11/2003 |
| WO | WO-2004/052368 A1 | 6/2004 |
| WO | WO-2005/007699 A2 | 1/2005 |
| WO | WO-2005/091853 A2 | 10/2005 |

OTHER PUBLICATIONS

Hauber et al., Hans-Peter; Increased expression of Interleukin-13 but not Interleukin-4 in cystic fibrosis patients. Journal of cystic fibrosis Dec. 2003, 2 (4) p. 189-194.*
Riccieri V. et al. Interleukin-13 in systemic sclerosis: relationship to nailfold capillaroscopy abnormalities. Clinical rheumatology (Belgium) May 2003, 22 (2) p. 102-106.*
Nathan N. et al., Plasma interleukin-4, interleukin-10, and interleukin-13 concentrations and complications after coronary artery bypass graft surgery. Journal of cardiothoracic and vascular anesthesia (United States) Apr. 2000, 14 (2) p. 150-160.*
Aguirre et al., Am. J. Cardiology, 63:1098-1102, May 1, 1989.*
Tsugiyasu Kanda et al., Jpn Heart J., vol. 45. pp. 183-193 (2004).
Arnon Blum et al., Annu. Rev. Med.,vol. 52 , pp. 15-27 (2001).
S. Till et al., Immunology, vol. 91, pp. 53-57 (1997).
Shau-Ku Huang et al., The Journal of Immunology, pp. 2688-2694 (1995).
Tomoaki Ohtsuka et al., The European Journal of Heart Failure, vol. 7, pp. 689-695, (2005).
Cariolou et al., "W01-P-006 HDL cholesterol, smoking and IL13 R130Q polymorphism are associated with myocardial infaction in Greek Cypriot males", Artherosclerosis Supplements, Elsevier, vol. 6, No. 1, p. 3 (Apr. 2005) XP005011187 (abstract).
Tang et al., "Changes of plasma IL-13 in patients with actue cerbral stroke", Chinese Journal of Neurology, vol. 35, No. 3 (Jun. 25, 2002), Elsevier Science Publishers, Amsterdam, NL, XP002381450.
Elnaggar et al., Eur. J. Immunol., vol. 35, No. 6, pp. 1995-2005 (Jun. 2005) XP002380811.

* cited by examiner

*Primary Examiner* — Lorraine Spector
(74) *Attorney, Agent, or Firm* — Birch, Stewart, Kolasch & Birch, LLP

(57) ABSTRACT

The present invention relates to use of interleukin-13 as a cardiovascular disease marker. The therapeutic composition and diagnostic composition of the invention for cardiovascular diseases are characterized by comprising an antibody to an interleukin-13 receptor and/or an antibody to interleukin-13.

4 Claims, 2 Drawing Sheets

INTERLEUKIN-13 AS A CARDIOVASCULAR DISEASE MARKER

FIELD OF THE INVENTION

The present invention relates to a therapeutic or diagnostic composition for cardiovascular diseases and a diagnostic kit for cardiovascular diseases.

BACKGROUND OF THE INVENTION

The number of patients with ischemic heart diseases such as angina and myocardial infarction and cardiovascular diseases such as heart failure has been rapidly increasing as a result of the westernization of people's life and the coming of aging society. Besides, the number of refractory cases resistant to drug-therapy has tended to increase. Therefore, discovering cardiovascular disease markers which are highly quantifiable, reproducible and yet simple, and developing novel methods of diagnosis or treatment are strongly demanded.

On the other hand, a great number of basic studies and clinical studies have made it clear that inflammatory cytokines such as interleukin-6 (IL-6) play an important role in the development and progress of cardiovascular diseases (Kanda T et al., Jpn Heart J., vol. 45, pp. 183-193 (2004); Blum A et al., Anu. Rev. Med., vol. 52, pp. 15-27 (2001)). However, the blood IL-6 level cannot be said sufficient as a marker for diagnosing the development or progress of cardiovascular diseases. Therefore, IL-6 has not been established as a diagnostic marker for cardiovascular diseases in actual clinical practice.

SUMMARY OF THE INVENTION

The problem for solution by the invention is to find out a useful diagnostic marker for cardiovascular diseases and, by using the finding, to provide a therapeutic or diagnostic composition for cardiovascular diseases and a diagnostic kit for cardiovascular diseases.

The present inventors have made intensive and extensive researches toward the solution of the above problem.

In the process of that activity, the present inventors have paid attention not to inflammatory cytokines such as IL-6 but to an allergic cytokine "interleukin-13 (IL-13)" which has never been reported so far in relation to cardiovascular diseases and treatment thereof, and examined its role in the development and progress of cardiovascular diseases.

As a result, the present inventors have found that blood IL-13 levels are increased in patients with cardiovascular diseases such as chronic heart failure and that blood IL-13 levels correlate with the severity of cardiovascular diseases. Further, the present inventors have demonstrated that IL-13 activates cytotoxic signals in vascular endothelial cells and that IL-13 receptor inhibition suppresses the cytotoxicity by IL-13 in vascular endothelial cells.

From the above-described findings, the present inventors have made it clear that IL-13 is useful as a marker for diagnosing cardiovascular diseases and for judging prognosis and treatment effect, and also demonstrated that inhibiting the effect of allergic cytokines including IL-13 leads to a novel method for treating cardiovascular diseases such as heart failure. Specifically, the inventors have found that the above-described problems can be solved at once by using an antibody to the receptor of the relevant allergic cytokine and/or an antibody to the relevant allergic cytokine. Thus, the present invention has been achieved.

The present invention relates to the following.
(1) A cardiovascular disease marker comprising interleukin-13.
(2) A diagnostic composition for cardiovascular diseases, comprising an antibody to interleukin-13.
(3) A therapeutic composition for cardiovascular diseases, comprising an antibody to an interleukin-13 receptor and/or an antibody to interleukin-13.
(4) A diagnostic kit for cardiovascular diseases, comprising an antibody to interleukin-13.
(5) A method of evaluating the state of cardiovascular diseases, comprising reacting a biological sample with an antibody to interleukin-13 to thereby detect interleukin-13, and evaluating the state of the cardiovascular diseases using the detection results as an indicator.

In the present invention, specific examples of cardiovascular diseases include heart failure and myocardial infarction.
(6) A method of treating cardiovascular diseases, comprising using an antibody to an interleukin-13 receptor and/or an antibody to interleukin-13.
(7) Use of an antibody to an interleukin-13 receptor and/or an antibody to interleukin-13 for preparing a pharmaceutical to be used for treating cardiovascular diseases.

DETAILED DESCRIPTION OF THE INVENTION

Figure 1:
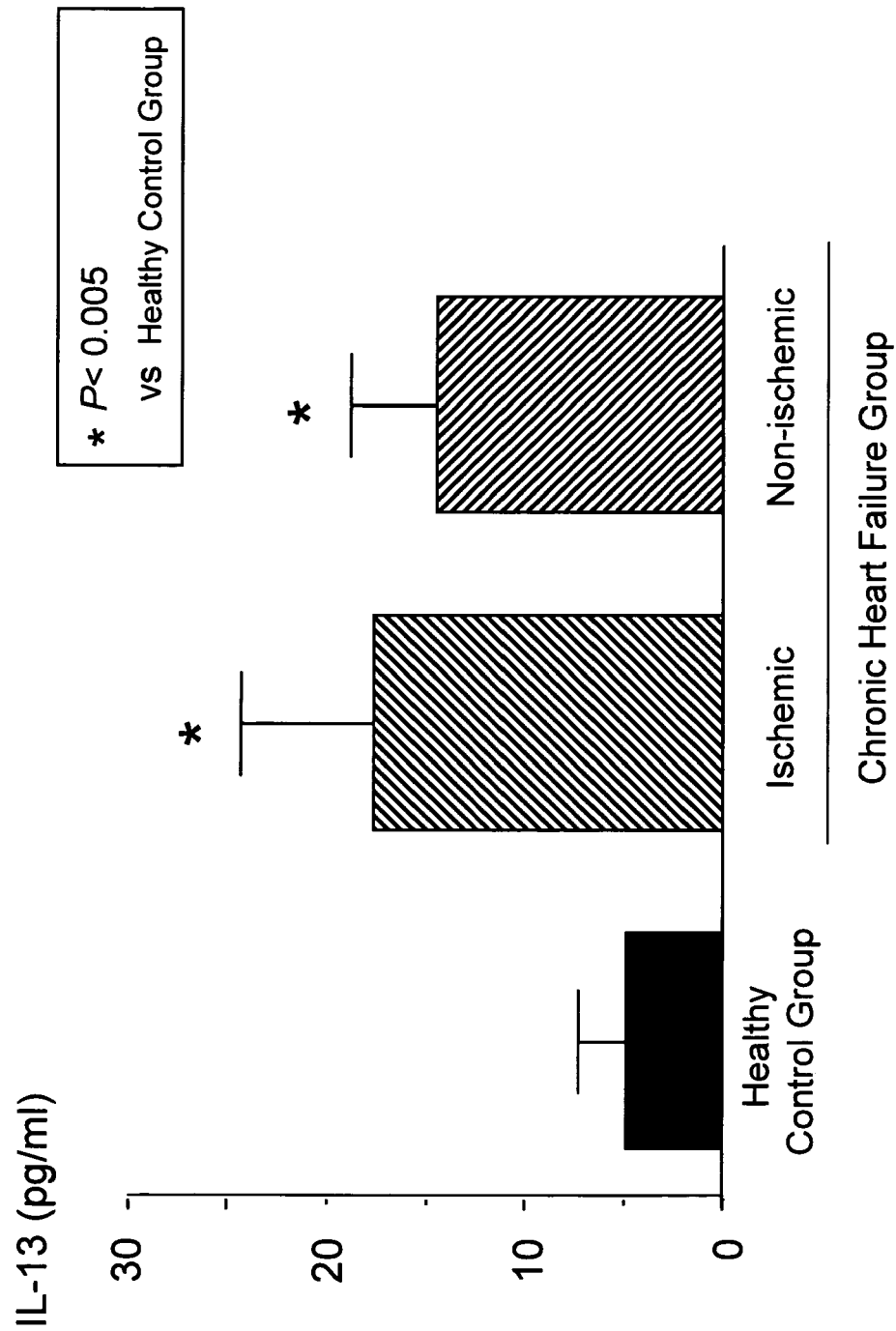
FIG. 1 is a graph showing blood levels of IL-13 in healthy persons and patients with chronic heart failure.

Hereinbelow, the present invention will be described in detail. It should be noted that the scope of the present invention is not limited to the following description and that modifications to the embodiments disclosed herein may be made appropriately without departure of the spirit of the invention.

The present specification encompasses the entire disclosure of the Japanese Patent Application No. 2005-44644 based on which the present application claims priority. All publications (e.g., prior art documents) and patent publications, patents and other patent documents cited herein are incorporated herein by reference in their entirety.

1. Outline

From the results of examination made by the present inventors, it is believed that blood IL-13 levels are useful for diagnosing diseases such as heart failure, judging therapeutic effect on such diseases, and judging prognosis of such diseases. Rise in blood IL-13 levels is also confirmed in cases of acute myocardial infarction and cases of acute heart failure. Since it is easy to measure blood IL-13 levels repeatedly even in clinic, blood IL-13 levels can be a useful diagnostic marker for cardiovascular diseases.

Further, the present inventors have found that IL-13 activates intracellular signals in vascular endothelial cells to thereby inhibit the survival and movement of the endothelial cells. It was also found that these cytotoxic effects of IL-13 on vascular endothelial cells are inhibited by IL-13 signal blockade using an anti-IL-13 receptor α subunit neutralizing antibody or an anti-IL-13 antibody. Therefore, it is believed that inhibiting the effect of allergic cytokines including IL-13 will lead to a novel method of treating cardiovascular diseases including heart failure.

2. Cardiovascular Diseases

The marker, the diagnostic composition, the therapeutic composition and the diagnostic kit of the invention are all used in relation to cardiovascular diseases. The target cardiovascular diseases include, but are not limited to, chronic or acute heart failure, ischemic heart diseases including myocardial infarction and angina, valvular disease, arrhythmia, and arteriosclerosis. Among all, heart failure and myocardial infarction are preferable; heart failure is more preferable; and chronic heart failure is still more preferable.

3. Therapeutic Composition

The therapeutic composition of the invention is, as described above, characterized by comprising an antibody to an interleukin-13 receptor (anti-IL-13 receptor antibody) and/or an antibody to interleukin-13 (anti-IL-13 antibody).

The present invention also encompasses a method of treating cardiovascular diseases characterized by using an anti-IL-13 receptor antibody and/or an anti-IL-13 antibody, and use of an anti-IL-13 receptor antibody receptor and/or an anti-IL-13 antibody for preparing a pharmaceutical to be used for treating cardiovascular diseases.

(1) Anti-IL-13 Receptor Antibody

Of the antibodies which may be contained in the therapeutic composition of the invention, anti-IL-13 receptor antibody may be prepared as described below.

(A) Preparation of Polyclonal Antibodies (i) Preparation of Antigen and Solution Thereof For the preparation of anti-IL-13 receptor antibody, first, a protein to be used as an immunogen (antigen) must be prepared and obtained.

As an antigenic protein, a purified IL-13 receptor may be used, but the antigenic protein is not limited to this. Other proteins may also be used. For example, a protein which consists of the amino acid sequence of an IL-13 receptor having deletion, substitution or addition of one to several amino acids and still has IL-13 receptor activity may be used. The amino acid sequence information about human IL-13 receptors may be obtained from GenBank Accession Nos. NM001560 and NM000640.

As a method for preparing a purified IL-13 receptor, a method may be used, for example, in which an IL-13 receptor is purified as an *Escherichia coli*-derived or baculovirus-derived recombinant protein.

Alternatively, commercial purified IL-13 receptors may be used. For example, human IL-13 Rα1/Fc chimera (R&D Systems), human IL-13 Rα2/Fc chimera (R&D Systems), and the like may be enumerated.

Subsequently, the thus obtained purified IL-13 receptor is dissolved in a buffer to prepare an antigen solution. At this point, if necessary, adjuvant may be added to perform immunization effectively. Specific examples of adjuvants useful in the invention include commercial Freund's complete adjuvant and Freund's incomplete adjuvant. These adjuvants may be used independently or in combination.

(ii) Immunization and Collection of Antisera

Immunization is performed by administering the above-described solution containing purified IL-13 receptor to a mammal (e.g., mouse, rat, rabbit or the like). The administration is performed mainly by intravenous, subcutaneous or intraperitoneal injection.

The dose of the antigen solution per time is not particularly limited. For example, the dose is adjusted so that preferably 2-500 μg, more preferably 10-100 μg of purified IL-13 receptor is administered per animal.

The administration interval is not particularly limited. Administration may be carried out at intervals of preferably several days to several weeks, more preferably 2 to 3 weeks. The number of times of administration is, for example, 2-10 times.

The sera (antisera) resultant from the above immunization may be collected preferably 1-28 days, more preferably 2-14 days after the final immunization. The antisera may be collected from the immunized animals according to conventional methods.

(iii) Selection of Antisera of Interest

From the antisera collected from the individual immunized animals, antisera of interest (i.e., antisera containing anti-IL-13 receptor antibody) are screened for.

The screening method is not particularly limited. For example, the screening may be performed by a known immunoassay according to conventional methods using the antisera collected and a purified IL-13 receptor or recombinant IL-13 receptor (produced in human-derived cultured fibroblast cells, Chinese hamster ovary cells, yeast cells or the like) or a mutant enzyme thereof as an antigen. As the immunoassay, labeled immunoassay or turbidometric immunoassay (TIA) may be used. The former is preferable. For example, enzyme immunoassay (EIA) such as ELISA, radioimmunoassay (RIA) or fluorescence immunoassay (FIA) may be used preferably. As a combination of labeled immunoassay with other separation method, Western blotting (combination with electrophoresis) may be used preferably. When Western blotting is used, the antigen used in the screening should be a mutant enzyme because the protein sample (the target for detection) is denatured with heat and a surfactant.

The anti-IL-13 receptor antibody contained in the antisera of interest obtained by the above-described screening is usually a polyclonal antibody. When purification of this antibody is necessary, it may be purified by conventional methods such as ammonium sulfate salting out, ion exchange chromatography, affinity chromatography, gel filtration or the like. These methods may be used independently or in an appropriate combination.

The reaction site in IL-13 receptor to which the above-described anti-IL-13 receptor antibody is capable of binding (i.e., capable of recognizing) is not particularly limited. For example, α subunit of IL-13 receptor is preferable. That is, anti-IL-13 receptor α subunit neutralizing antibody is preferable as the anti-IL-13 receptor antibody.

(B) Preparation of Monoclonal Antibodies (i) Preparation of Antigen and Solution Thereof Antigen and solution thereof may be prepared in the same manner as described above for the preparation of polyclonal antibodies.

(ii) Immunization and Collection of Antibody-Producing Cells

Immunization method, the dose of antigen solution, the administration interval and the number of times of administration may be selected in the same manner as described above for the preparation of polyclonal antibodies.

The anti-IL-13 receptor antibody-producing cells (antibody-producing cells) obtained by the above-described immunization are collected, for example, 1-14 days after the final immunization, more preferably 2-4 days thereafter.

As antibody-producing cells, splenic cells, lymph node cells (especially, local lymph node cells), peripheral blood cells, and the like may be enumerated preferably. Among all, splenic cells or local lymph node cells (e.g., popliteal lymph node cells) are more preferable.

(iii) Cell Fusion

Fusion cells (hybridomas) can be obtained by performing cell fusion between the collected antibody-producing cells and myeloma cells.

As the myeloma cell, a commonly available cell strain derived from a mammal such as mouse may be used. Specifically, a preferable cell strain to be used in the invention has drug selectivity, cannot survive in HAT selection medium (containing hypoxanthine, aminopterin and thymidine) in unfused conditions, and can survive there only after fusion to antibody-producing cells. Specific examples of mouse myeloma cells useful in the invention include PAI, P3X63-Ag.8.U1(P3U1) and NS-I.

The above-described cell fusion is carried out by mixing antibody-producing cells with myeloma cells in an animal cell culture medium (such as serum-free RPMI-1640) for fusion reaction, The mixing ratio of antibody-producing cells to myeloma cells is, for example, 5:1.

Generally, fusion reaction is performed preferably in the presence of a cell fusion promoter. As the cell fusion promoter, polyethylene glycol with an average molecular weight of 1,000-6,000 daltons or the like may be used. Alternatively, it is also possible to fuse antibody-producing cells and myeloma cells in a commercial cell fusion device utilizing electric stimulation (e.g., electroporation).

Cells after fusion reaction are cultured, for example, in HAT selection medium. After the culture, cells which have grown in HAT selection medium are fusion cells (hybridomas).

(iv) Selection of Hybridomas of Interest and Cloning Thereof

Hybridomas of interest, i.e., hybridomas producing anti-IL-13 receptor antibody are screened for from the hybridomas obtained by the above-described culture. Specifically, those hybridomas whose culture supernatant contains the anti-IL-13 receptor antibody of interest are screened for.

The screening method is not particularly limited. For example, the screening may be performed by a known immunoassay according to conventional methods using an aliquot of the culture supernatant and a purified IL-13 receptor or recombinant IL-13 receptor (produced in human-derived cultured fibroblast cells, Chinese hamster ovary cells, yeast cells or the like) or a mutant enzyme thereof as an antigen. As the immunoassay, labeled immunoassay or turbidometric immunoassay (TIA) may be used. The former is preferable. For example, enzyme immunoassay (EIA) such as ELISA, radioimmunoassay (RIA) or fluorescence immunoassay (FIA) may be used preferably. As a combination of labeled immunoassay with other separation method, Western blotting (combination with electrophoresis) may be used preferably. When Western blotting is used, the antigen used in the screening should be a mutant enzyme because the protein sample (the target for detection) is denatured with heat and a surfactant.

The anti-IL-13 receptor antibody contained in the culture supernatants of hybridomas of interest obtained by the above-described screening is an antibody which is obtained before the cloning of hybridomas. Alternatively, the antibody may be an antibody consisting of a single molecule (monoclonal antibody).

The reaction site in IL-13 receptor to which the above-described anti-IL-13 receptor antibody is capable of binding (i.e., capable of recognizing) is not particularly limited.

Cloning of the hybridomas of interest by the above-described screening, that is, the establishment of monoclonal antibody-producing cell strains can be performed generally by selecting single cell-derived colonies by the limiting dilution culture method or the like.

(v) Collecting of Monoclonal Antibodies

The method for collecting monoclonal antibodies from the hybridomas obtained by the above-described cloning is not particularly limited. Generally, a cell culture method or abdominal dropsy formation method may be used.

In the cell culture method, the hybridoma cells obtained by the above cloning are cultured in an animal cell culture medium at 37° C. under 5% $CO_2$ for 7 to 14 days. Then, the antibody of interest can be obtained from the culture supernatant.

In the abdominal dropsy formation method, the hybridoma cells are administered into the abdominal cavity of an allogenic animal (approx. $1 \times 10^6$ cells/animal) to the mammal from which the myeloma cell used in the cell fusion derived, to thereby expand the hybridoma cells greatly. Seven to fourteen days thereafter, the abdominal dropsy or serum is collected to obtain the antibody of interest therefrom.

When purification of antibodies is necessary in either of the cell culture method or the abdominal dropsy formation method, antibodies may be purified by conventional methods such as ammonium sulfate salting out, ion exchange chromatography, affinity chromatography or gel filtration, or a combination of these methods.

(2) Anti-IL-13 Antibody

Of those antibodies which can be contained in the therapeutic composition of the invention, anti-IL-13 antibody may be prepared in the same manner as described above for the preparation of anti-IL-13 receptor antibody except that the procedures described in "Preparation of Antigen and Solution Thereof" above is replaced with the procedures described below.

(i) Preparation of Antigen and Solution Thereof

For the preparation of anti-IL-13 antibody, first, a protein to be used as an immunogen (antigen) must be prepared and obtained.

As an antigenic protein, a purified IL-13 may be used, but the antigenic protein is not limited to this. Other proteins may also be used. For example, a protein which consists of the amino acid sequence of IL-13 having deletion, substitution or addition of one to several amino acids and still has IL-13 activity may be used. The amino acid sequence information about human IL-13 may be obtained from GenBank Accession No. NM002188.

As a method for preparing a purified IL-13, a method may be used, for example, in which IL-13 is purified as an *Escherichia coli*-derived or baculovirus-derived recombinant protein.

Alternatively, commercial purified IL-13 may be used. For example, human IL-13 (R&D Systems) may be enumerated.

Subsequently, the thus obtained purified IL-13 is dissolved in a buffer to prepare an antigen solution. Subsequent immunization procedures are the same as described above.

(3) Ratio of the Antibody

In the therapeutic composition of the invention, the ratio of the antibody is not particularly limited for both anti-IL-13 receptor antibody and anti-IL-13 antibody. For example, when the composition is a therapeutic composition for cardiovascular diseases, the ratio of anti-IL-13 receptor antibody is preferably 0.1-20 weight %, more preferably 1-5 weight %; and the ratio of anti-IL-13 antibody is preferably 0.1-20 weight %, more preferably 1-5 weight %.

(4) Other Components

The therapeutic composition of the invention may comprise components other than anti-IL-13 receptor antibody and/or anti-IL-13 antibody within a range that would not damage the effect of the invention remarkably, and the other components are not particularly limited. When the composition is a therapeutic composition for cardiovascular diseases, the composition may comprise such components as described later that are generally used in pharmaceutical manufacturing.

(5) Administration Methods and Dose Levels

The therapeutic composition of the invention (preferably, therapeutic for cardiovascular diseases) may be administered into the body by known methods such as parenteral administration or oral administration. Preferably, the composition is administered parenterally.

Preparations to be used in these administration methods (parenteral preparations and oral preparations) may be formulated by conventional methods appropriately selecting and using excipients, fillers, extenders, binders, wetting agents, disintegrants, lubricants, surfactants, dispersants, buffers, preservatives, dissolution aids, antiseptics, flavoring agents, analgesics, stabilizers, isotonizing agents, etc. which are generally used in pharmaceutical manufacturing.

The dose level of the therapeutic composition of the invention may be selected in a wide range considering the ratios of the active ingredients (anti-IL-13 receptor antibody and/or anti-IL-13 antibody) in the preparations and also considering the age and body weight of the patient to be treated, kind of disease and the degree of progress, route of administration, number of times of administration (per day), period of administration and the like.

Hereinbelow, use of the therapeutic composition of the invention as a parenteral preparation and use of the same as an oral preparation will be described specifically.

When the composition is used as a parenteral preparation, generally, the form is not particularly limited. For example, the preparation may be any one of intravenous injections (including drips), intramuscular injections, intraperitoneal injections, subcutaneous injections, suppositories, and so forth. When preparations are various injections, they may be provided in the form of unit dosage ampoules or multi-administration containers, or in the form of freeze-dried powder which is re-dissolved at the time of use. The parenteral preparation may comprise, depending on its form, various excipients and additives known in the art within the range that will not damage the effect of the active ingredients. For example, in the case of various injections, water, glycerol, aliphatic polyalcohols such as propylene glycol and polyethylene glycol may be enumerated.

The dose level of parenteral preparations (per day) is not particularly limited. When the preparations are various injections, the dose level is selected so that the above-described active ingredient is administered at a dose of preferably 1-20 mg, more preferably 1-10 mg per kg bodyweight of the patient to be treated.

When the composition is used as an oral preparation, generally, the form is not particularly limited. For example, the preparation may be any one of tablets, capsules, granules, powders, pills, troches, internal solutions, suspensions, emulsions, syrups, and so forth. Alternatively, the preparation may be in the form of a dry product which is re-dissolved at the time of use. The oral preparation may comprise, depending on its form, various excipients and additives known in the art within the range that will not damage the effect of the active ingredients. For example, binders (e.g., syrup, gum arabic, gelatin, sorbitol, tragacanth, polyvinyl pyrrolidon, etc.), fillers (e.g., lactose, sugar, corn starch, potato starch, calcium phosphate, sorbitol, glycine, etc.), lubricants (e.g., magnesium stearate, talc, polyethylene glycol, silica, etc.), disintegrants (e.g., various starches, etc.) and wetting agents (e.g., sodium lauryl sulfate, etc.) may be enumerated.

The dose level of oral preparations (per day) is selected so that the above-described active ingredient is administered at a dose of preferably 1-100 mg, more preferably 1-10 mg per kg bodyweight of the patient to be treated.

The ratio of the active ingredient in oral preparations is not limited. The ratio may be appropriately selected considering the number of times of administration per day.

4. Diagnostic Composition

The diagnostic composition of the invention is, as described earlier, a composition characterized by comprising an antibody to interleukin-13 (anti-IL-13 antibody).

Preferably, the diagnostic composition of the invention is a diagnostic agent for cardiovascular diseases.

The present invention also encompasses a method of diagnosing cardiovascular diseases characterized by using anti-IL-13 antibody; and use of anti-IL-13 antibody for preparing a diagnostic composition for cardiovascular diseases.

(1) Anti-IL13 Antibody

The above description made for the anti-IL-13 antibody contained in the therapeutic composition of the invention is applicable to the anti-IL-13 antibody contained in the diagnostic composition of the invention.

(2) Ratio of the Antibody

In the diagnostic composition of the present invention, the ratio of the anti-IL-13 antibody is not particularly limited. For example, when the composition is a diagnostic agent for cardiovascular diseases, the ratio of the anti-IL-13 antibody is preferably 1-100 weight %, more preferably 10-100 weight %.

(3) Other Components

The diagnostic composition of the invention may comprise components other than the anti-IL-13 antibody within a range which would not damage the effect of the invention remarkably, and the other components are not particularly limited. When the composition is a diagnostic agent for cardiovascular diseases, the composition may comprise, for example, a reagent for detecting a primary antibody and a substrate for color development.

(4) Detection and Quantitative Determination of IL-13

The diagnostic composition of the invention (preferably, diagnostic agent for cardiovascular diseases) is used to detect and quantitatively determine IL-13 in blood samples. By comparing the results with the detection results in healthy persons, it is possible to judge (diagnose) the possibility of cardiovascular diseases and the severity of conditions. Further, by monitoring the IL-13 levels in a same patient periodically, it is also possible to judge the state of cardiovascular diseases.

(i) Detection of IL-13

Blood taken as a test sample is pre-treated for serum separation and then, generally, diluted with a sample buffer at 1- to −100-fold. As the sample buffer, phosphate buffered saline or the like may be used.

The test sample thus treated is contacted with the diagnostic composition of the invention to react with an anti-IL-13 antibody (generally, a monoclonal antibody is preferable).

The reaction between the test sample and the anti-IL-13 antibody is performed at 10-30° C. (preferably 15-25° C.) for 60-180 minutes (preferably 90-120 minutes).

The detection of IL-13 may be performed by using a known immunoassay. As the immunoassay, labeled immunoassay or turbidometric immunoassay (TIA) may be used. The former is preferable. For example, enzyme immunoassay (EIA) such as ELISA, radioimmunoassay (RIA) or fluorescence immunoassay (FIA) may be used preferably. As a combination of labeled immunoassay with other separation method, Western blotting (combination with electrophoresis) may be used preferably. Among all, ELISA and/or Western blotting is preferable. Alternatively, one or a combination of two or more anti-IL-13 monoclonal antibodies may be used in a combination of two or more immunoassays to perform excellent detection with still higher sensitivity and reliability.

(ii) Quantitative Determination of IL-13

The method of quantitative determination of IL-13 is not particularly limited. Preferably, the amount of IL-13 contained in a test sample is determined from a calibration curve based on the relation between the amount of antigen (antigen concentration: IL-13 concentration) and the detected levels thereof. The calibration curve is prepared in advance based on the detected levels (detection data) obtained using purified IL-13 as an antigen and the above-describe anti-IL-13 antibody. Briefly, data of detected levels against antigen concentration are obtained by the same immunoassay method (ELISA, Western blotting, etc.) as described above as detection method, followed by preparation of a calibration curve based on the data. By comparing the calibration curve with the actual detected levels (actually measured levels), the amount of IL-13 in the test sample can be obtained.

Alternatively, the quantitative determination or detection of IL-13 may be performed with a commercial kit.

(iii) Evaluation of Cardiovascular Diseases

In the present invention, the state of cardiovascular diseases may be evaluated using the IL-13 level quantitatively determined or detected as described above as an indicator. The term "evaluating the state of cardiovascular diseases" means judging the presence or absence of the development of cardiovascular diseases, the degree of progress thereof, the severity thereof, the treatment responsiveness thereof, the prognosis thereof, and so forth. The evaluation may be performed using the IL-13 levels in combination with subjective symptoms and data from various diagnostic imaging methods. Although cardiovascular diseases may be evaluated by measuring IL-13 at a frequency of one or two times a year as conducted in periodic medical examination, it is preferable to evaluate the state of cardiovascular diseases comprehensively by monitoring the transition of IL-13 levels periodically. With such an evaluation method, it becomes possible to make the following judgments: when IL-13 level exceeds a specific level, it is judged as heart failure requiring treatment; when IL-13 level decreases in cases where cardiovascular diseases are now being treated, it is judged that the treatment is successful; and when IL-13 value has exceeded a specific level and remains at high revels, it is judged that life prognosis is poor.

5. Diagnostic Kit

In the diagnosis of cardiovascular diseases as described above, a diagnostic kit for cardiovascular diseases may be used. For example, a kit comprising the above-described anti-IL-13 antibody as a component may be given.

In the above-described kit, it is preferred that the anti-IL-13 antibody be provided in the state of a solution considering stability (preservation property) and easiness for use.

The above-described kit may comprise other components in addition to the anti-IL-13 antibody. For example, the kit may comprise a reagent for detecting a primary antibody, a substrate for color development, or the like. Especially when the kit is intended to perform the detection by ELISA, a primary antibody and a substrate for color development may be enumerated further as the other components. When the kit is intended to perform the detection by Western blotting, a primary antibody and a substrate for color development may be enumerated further as the other components.

The above-described kit may be any kit as long as it comprises the above-described anti-IL-13 antibody as a component. Therefore, the kit may or may not comprise all the components necessary for diagnosis of cardiovascular diseases (detection of IL-13) together with the anti-IL-13 antibody.

Hereinbelow, the present invention will be described in more detail with reference to the following Example. However, the present invention is not limited to this Example.

EXAMPLE 1

Detection of IL-13 in Patients with Chronic Heart Failure (1) Method

Subjects were 66 chronic heart failure patients in Saga University Hospital and related facilities thereof. The particulars are as follows.

Ischemic, chronic heart failure patients with myocardial infarction as a pre-existing heart disease: 27 cases Non-ischemic, chronic heart failure patients with non-ischemic heart diseases including dilated cardiomyopathy as pre-existing heart diseases: 39 cases Healthy control group: 14 cases Blood IL-13 levels were measured as follows. Peripheral venous blood samples were taken to obtain sera. Then, serum IL-13 levels were measured with an ELISA kit (BioSource).

(2) Results

As a result of examination of blood IL-13 levels in chronic heart failure patients, both the group of ischemic, chronic heart failure patients with myocardial infarction as a pre-existing heart disease and the group of non-ischemic, chronic heart failure patients with non-ischemic heart diseases including dilated cardiomyopathy as a pre-existing heart disease(s) showed significantly higher blood IL-13 levels than the healthy control group (FIG. 1).

(Ischemic, chronic heart failure patient group: 17.7±16.7; non-ischemic, chronic heart failure patient group: 13.7±14.1; healthy control group: 4.9±2.4 pg/ml, P<0.005)

Figure 2:
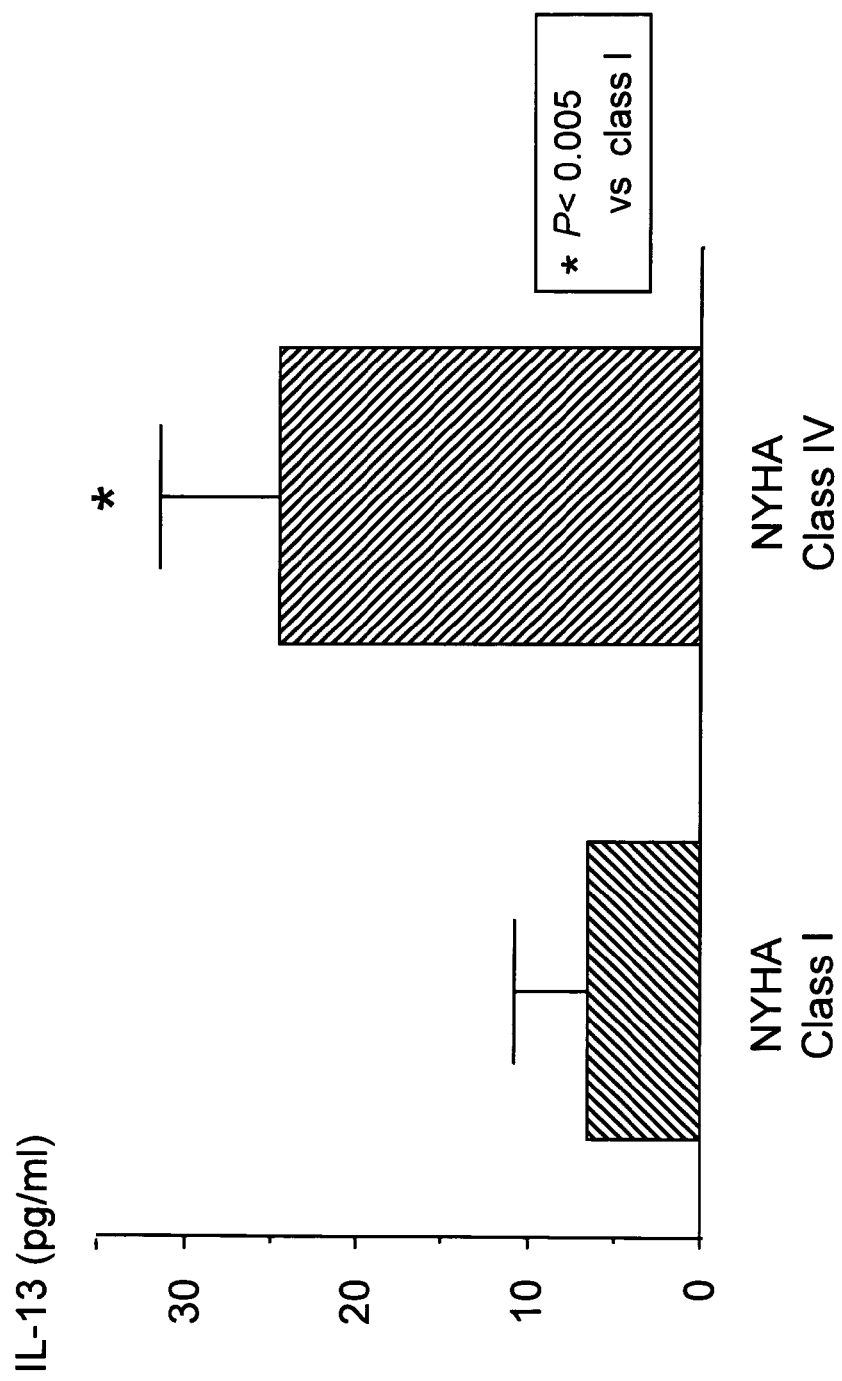
FIG. 2 is a graph showing blood levels of IL-13 in patients with chronic heart failure.

Further, correlation between blood IL-13 levels and a heart failure severity classification based on subjective symptoms (NYHA classification) was examined. According to the NYHA classification, severity is classified into 4 stages from class I (lightest) to class IV (most severe) based on subjective symptoms. In chronic heart failure patients, class IV patients showed significantly higher blood IL-13 levels than class I patients, indicating correlation with the heart failure severity based on subjective symptoms (FIG. 2).

(NYHA class I (light) vs. NYHA class IV (severe): 6.5±4.3 vs. 24.6±16.9 pg/ml, P<0.005)

Further, blood IL-13 levels in chronic heart failure patients showed positive correlation with blood BNP levels and negative correlation with the heart function evaluated by cardiac ultrasonography in chronic heart failure patients.

In cultured vascular endothelial cells, IL-13 activated JAK2 and STAT6, and this activation was inhibited by anti-IL-13 receptor α subunit neutralizing antibody.

In cultured vascular endothelial cells, IL-13 inhibited the survival and movement of the endothelial cells.

From these findings, it has been demonstrated that IL-13 is a useful marker for cardiovascular diseases such as heart failure.

What is claimed is:

1. A method of evaluating the state of a chronic heart failure in a subject diagnosed with said chronic heart failure, comprising:

obtaining a blood sample from said subject, detecting interleukin-13 in serum of the sample using an antibody to interleukin-13, determining pg of interleukin-13/ml serum in said sample, correlating the determined pg of interleukin-13/ml serum with said state of said chronic heart failure, wherein
if the determined pg of interleukin-13/ml serum in the sample is 24.6 pg of interleukin-13/ml serum or above the state of chronic heart failure is NYHA class IV.

2. A method of evaluating the state of a chronic heart failure in a subject diagnosed with chronic heart failure, comprising:
obtaining a blood sample from said subject,
determining pg of interleukin-13/ml serum in said sample,
comparing pg of interleukin-13/ml serum in said sample to a baseline level developed from healthy person samples, wherein pg of interleukin-13/ml serum is greater than said baseline level, and
if the determined pg of interleukin-13/ml serum in the sample is 24.6 pg of interleukin-13/ml serum or above the state of chronic heart failure is NYHA class IV.

3. A method of evaluating the state of a chronic heart failure, comprising:
diagnosing a subject with chronic heart failure using a diagnostic imaging method, and
obtaining a blood sample from said subject,
detecting interleukin-13 in serum of the sample using an antibody to interleukin-13,
determining pg of interleukin-13/ml serum,
correlating the determined pg of interleukin-13/ml serum with said state of said chronic heart failure,
wherein
if the determined pg of interleukin-13/ml serum in the sample is 24.6 pg of interleukin-13/ml serum or above the state of chronic heart failure is NYHA class IV.

4. The method of claim 3, wherein the diagnostic imaging method is ultrasonography.

* * * * *